United States Patent
Whyte et al.

(10) Patent No.: US 9,308,024 B2
(45) Date of Patent: Apr. 12, 2016

(54) TISSUE DEBRIDEMENT SYSTEMS AND METHODS

(75) Inventors: David George Whyte, Wareham (GB); Keith Patrick Heaton, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 191 days.

(21) Appl. No.: 13/042,226

(22) Filed: Mar. 7, 2011

(65) Prior Publication Data

US 2011/0224691 A1 Sep. 15, 2011

Related U.S. Application Data

(60) Provisional application No. 61/312,940, filed on Mar. 11, 2010.

(51) Int. Cl.
*A61B 17/54* (2006.01)
*A61B 17/3203* (2006.01)
(Continued)

(52) U.S. Cl.
CPC ........... *A61B 17/545* (2013.01); *A61B 17/3203* (2013.01); *B24C 1/003* (2013.01); *B24C 7/0061* (2013.01); *A61B 2017/320004* (2013.01); *A61B 2017/32035* (2013.01)

(58) Field of Classification Search
CPC ...... A61B 17/3203; A61B 17/32037; A61B 17/545; A61B 2017/32032; A61B 2017/32035; B24C 7/0007; B24C 7/0046; B24C 7/0076
USPC ......... 606/131, 132, 159, 167–170, 110–115; 433/84, 88; 451/56, 75, 38, 90, 91, 96, 451/102, 99; 604/289, 290, 140, 69, 70, 72, 604/73, 313, 150, 22, 506, 131, 27, 35, 149, 604/43, 23–26, 518, 28; 222/192, 630; 600/104; 83/177
See application file for complete search history.

(56) References Cited

U.S. PATENT DOCUMENTS

| 1,355,846 | A | 10/1920 | Rannells |
| 2,547,758 | A | 4/1951 | Keeling |

(Continued)

FOREIGN PATENT DOCUMENTS

| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986);pp. 94-96 (certified translation.

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

(Continued)

*Primary Examiner* — Jocelin Tanner

(57) ABSTRACT

Systems, methods, and apparatuses for debriding a tissue site, such as a wound, involve using solid $CO_2$ particles and reduced pressure to cut and remove undesired tissue in a controlled manner. The system may urge the undesired tissue into a treatment cavity and then cut the undesired tissue with impinging $CO_2$ particles. The $CO_2$ particles sublime into a gas and present little or no mess. Other systems, methods, and apparatuses are presented.

10 Claims, 4 Drawing Sheets

(51) Int. Cl.
    *B24C 1/00*         (2006.01)
    *B24C 7/00*         (2006.01)
    *A61B 17/32*      (2006.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,690,672 A * | 9/1987 | Veltrup | 604/43 |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,037,432 A * | 8/1991 | Molinari | 606/131 |
| 5,086,170 A | 2/1992 | Luheshi et al. | |
| 5,092,858 A | 3/1992 | Benson et al. | |
| 5,094,615 A * | 3/1992 | Bailey | 433/88 |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,318,518 A * | 6/1994 | Plechinger et al. | 604/43 |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,496,267 A * | 3/1996 | Drasler et al. | 604/22 |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,934,904 A * | 8/1999 | Elrod et al. | 433/88 |
| 5,944,686 A * | 8/1999 | Patterson et al. | 604/22 |
| 6,071,267 A | 6/2000 | Zamierowski | |
| 6,083,001 A * | 7/2000 | Deardon et al. | 433/88 |
| 6,096,001 A * | 8/2000 | Drasler et al. | 604/22 |
| 6,135,116 A | 10/2000 | Vogel et al. | |
| 6,235,039 B1 * | 5/2001 | Parkin et al. | 606/131 |
| 6,241,747 B1 | 6/2001 | Ruff | |
| 6,264,666 B1 | 7/2001 | Coleman et al. | |
| 6,287,316 B1 | 9/2001 | Agarwal et al. | |
| 6,345,623 B1 | 2/2002 | Heaton et al. | |
| 6,375,635 B1 * | 4/2002 | Moutafis et al. | 604/43 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,726,693 B2 | 4/2004 | Weber et al. | |
| 6,814,079 B2 | 11/2004 | Heaton et al. | |
| 7,175,605 B2 * | 2/2007 | Tiedtke et al. | 604/27 |
| 2002/0058952 A1 * | 5/2002 | Weber et al. | 606/131 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0092920 A1 * | 5/2004 | Rozenshpeer | 606/22 |
| 2004/0121711 A1 | 6/2004 | Opel | |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |

(56) References Cited

FOREIGN PATENT DOCUMENTS

| WO | WO 97/18007 | 5/1997 |
|---|---|---|
| WO | WO 99/13793 | 3/1999 |
| WO | WO 02/38125 A2 | 5/2002 |

OTHER PUBLICATIONS

James H. Blackburn, II, MD, et al; "Negative-Pressure Dressings as a Bolster for Skin Grafts"; Annals of Plastic Surgey, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, Md., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Osinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 pages English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinović, V. Đukić, Z. Maksimović, Đ. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
International Search Report and Written Opinion date mailed May 30, 2011; PCT International Application No. PCT/US2011/027578.
Leff et al, "The Effect of Local Cooling on Pain Perception during Infiltration of local Anaesthetic Agents, a Prospective Randomised Controlled Trial" Anaesthesia, vol. 62, Issue 7, pp. 677-682.
Research: Cold comfort; Cooling may offer new way to alleviate chronic pain, Sep. 20, 2006; http://www.wellcome.ac.uk/News/2006News/WTX035276.htm.
Smith & Nephew, Versajet Hydrosurgery System, The cleaner way to operate, www.huidziekten.nl/woundcare/smithnephew/versajet.pdf, [date unknown].
Cold Jet, Dry Ice Blast Cleaning, www.coldjet.com/media/en/pdf/Cold_Jet_Blasting.pdf, [date unknown].
On Air magazine, Tough, ice cold and with real pressure—cleaning with dry ice, No. 2, Feb. 2007.
Brandsson et al, "Postoperative Analgesic Effects of an External Cooling System and Intra-Articular Bupivacaine/Morphine after Arthoscopic Cruciate Ligament Surgery", Abstract, Knee Surg Sports Traumatol Arthrosc., 1996; 4(4):200-5.

* cited by examiner

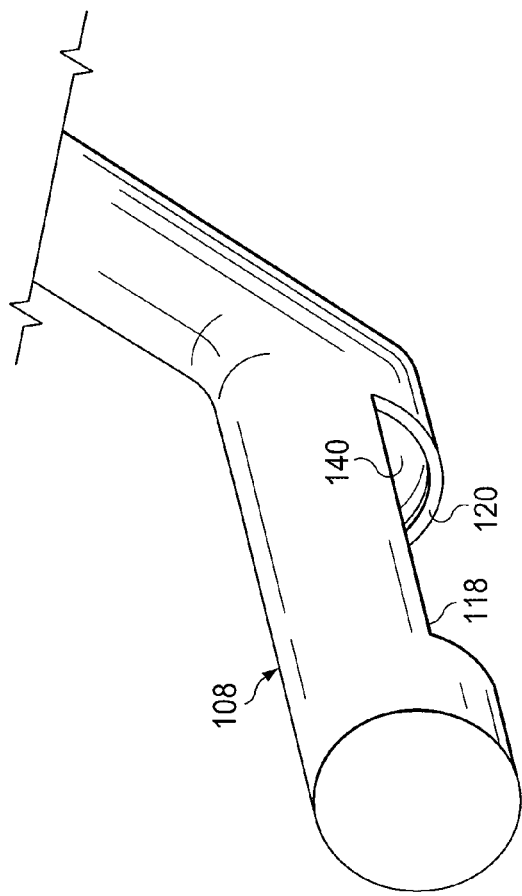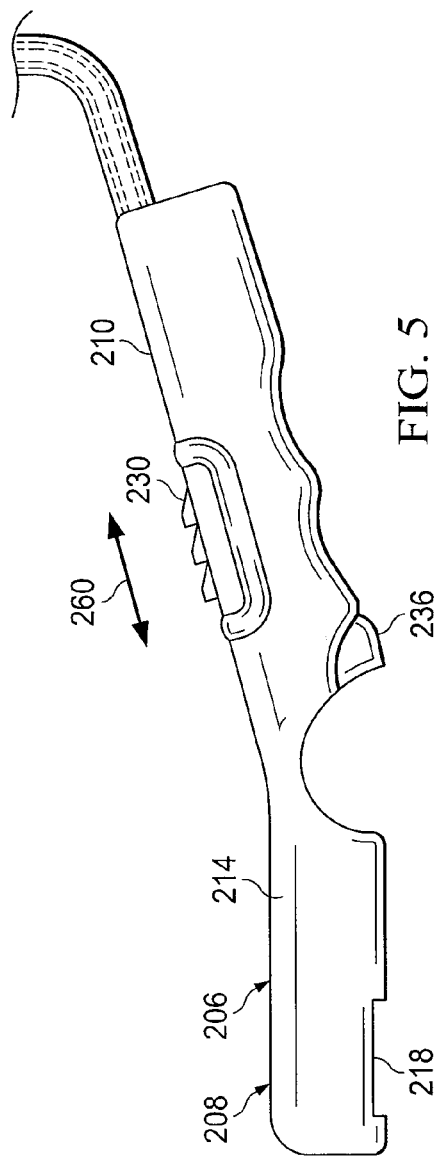

TISSUE DEBRIDEMENT SYSTEMS AND METHODS

RELATED APPLICATION

The present invention claims the benefit, under 35 USC §119(e), of the filing of U.S. Provisional Patent Application Ser. No. 61/312,940, entitled "Tissue Debridement Systems and Methods," filed 11 Mar. 2010, which is incorporated herein by reference for all purposes.

BACKGROUND

The present invention relates generally to medical treatment systems, and more particularly, to tissue debridement systems and methods.

Necrotic tissue may retard wound healing. As such, it may at times be desirable to remove necrotic tissue. The therapeutic intervention for necrotic tissue in the wound is debridement. A number of general approaches exist for debridement, e.g., mechanical, enzymatic or chemical, sharp, biosurgical, and autolytic. Mechanical methods of debridement may be painful and require a high level of skill to prevent damage to healthy tissue. Moreover, some mechanical systems create extensive debris that is propelled in numerous directions.

SUMMARY

According to one illustrative, non-limiting embodiment, a system for removing undesired tissue from a tissue site of a patient includes a working gas supply source for supplying a working gas and a $CO_2$ source for supplying solid $CO_2$ particles. The system may further include a reduced-pressure source for supplying reduced pressure. The system also includes a supply conduit fluidly coupled to the working gas supply source and the $CO_2$ source for receiving the working gas and solid $CO_2$ particles. The system further includes a treatment head fluidly coupled to the supply conduit for receiving the working gas and solid $CO_2$ particles and delivering the working gas and solid $CO_2$ particles to the tissue site at a desired location. An extraction conduit is fluidly coupled to the treatment head and fluidly coupled to the reduced-pressure source, where the latter is present. The system is configured such that the solid $CO_2$ particles impinge upon at least a portion of the undesired tissue to remove undesired tissue, and the extraction conduit carries away the undesired tissue under reduced pressure.

According to another illustrative, non-limiting embodiment, a method of debriding undesired tissue from a tissue site includes delivering solid $CO_2$ particles to the undesired tissue so as to cut the undesired tissue. The $CO_2$ particles are allowed to undergo sublimation to produce a $CO_2$ gas. The method further includes removing the $CO_2$ gas and the undesired tissue that has been cut by the solid $CO_2$ particles.

According to another illustrative, non-limiting embodiment, a method of manufacturing a system for removing undesired tissue from a tissue site of a patient includes the steps of: providing a working gas supply source for supplying a working gas; providing a $CO_2$ source for supplying solid $CO_2$ particles; and providing a reduced-pressure source for supplying reduced pressure. The method further includes forming a treatment head and fluidly coupling the working gas supply source and the $CO_2$ source to the treatment head. The working gas and solid $CO_2$ particles are delivered to the treatment head. The treatment head is configured to deliver the working gas and solid $CO_2$ particles to the tissue site at a desired location. The method further includes fluidly coupling the treatment head to a reduced-pressure source with an extraction conduit. The system is configured to deliver the solid $CO_2$ particles to the undesired tissue so as to remove the undesired tissue, and to transport the undesired tissue under reduced pressure away from the tissue site.

According to another illustrative, non-limiting embodiment, a system for removing undesired tissue from a tissue site of a patient includes a working gas supply source for supplying a working gas, a $CO_2$ source for supplying solid $CO_2$ particles, and a supply conduit fluidly coupled to the working gas supply source and the $CO_2$ source for receiving the working gas and solid $CO_2$ particles. The system further includes a treatment head coupled to the supply conduit for receiving the working gas and solid $CO_2$ particles and delivering the working gas and solid $CO_2$ particles to the tissue site at a desired location. The system is configured so that the solid $CO_2$ particles impinge upon at least a portion of the undesired tissue to remove undesired tissue.

Other features and advantages of the illustrative embodiments will become apparent with reference to the drawings and detailed description that follow.

BRIEF DESCRIPTION OF THE DRAWINGS

FIG. 2 is a schematic, perspective view of a portion of the illustrative system of FIG. 1 showing a portion of a treatment head;

FIG. 5 is a schematic, side view of an illustrative treatment member for removing undesired tissue.

DETAILED DESCRIPTION

Figure 1:
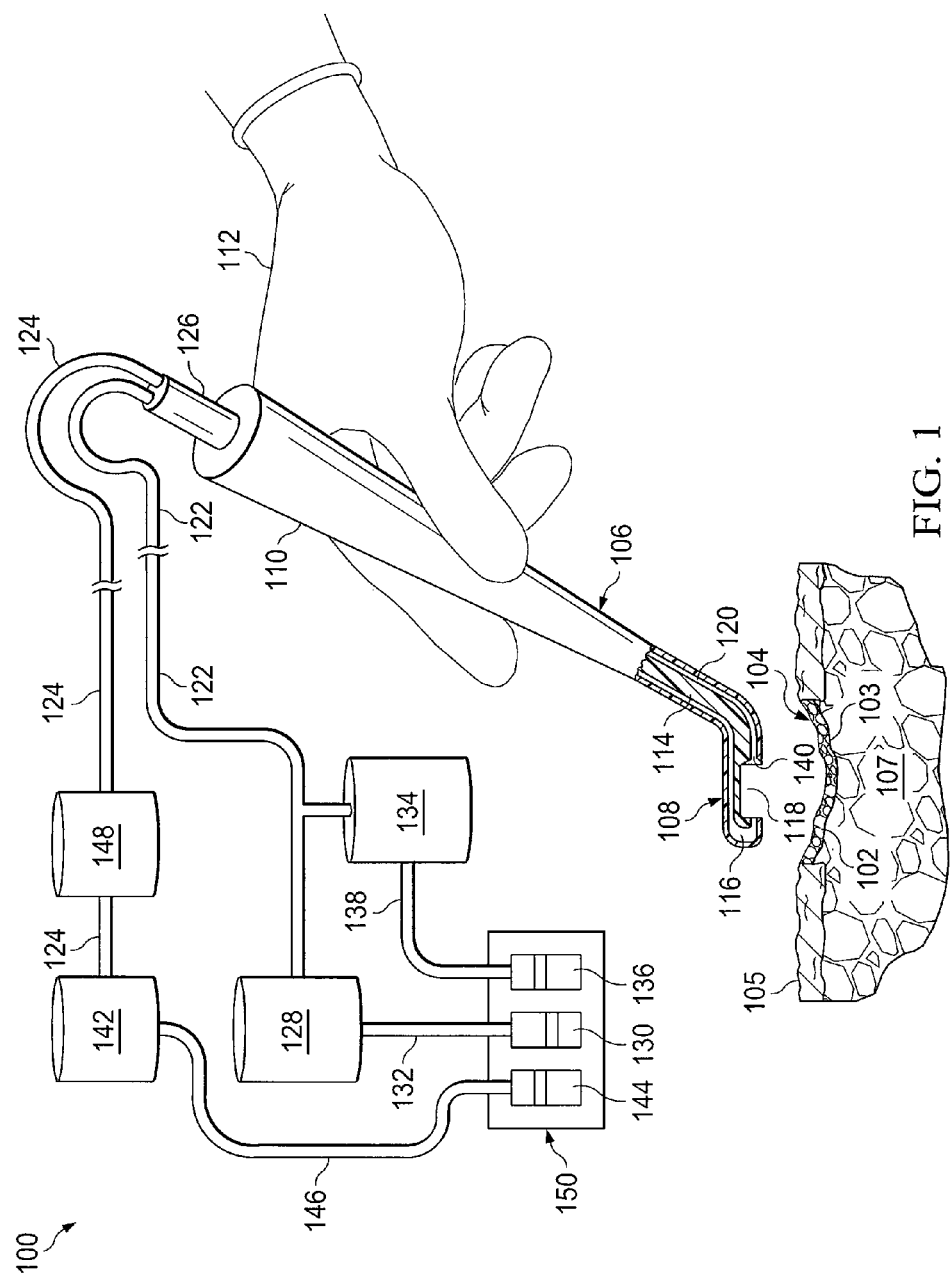
FIG. 1 is a schematic diagram with a portion shown in cross section and a portion shown in perspective view of an illustrative system for removing undesired tissue from a tissue site of a patient.

In the following detailed description of the non-limiting, illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Referring now to FIGS. 1-4, an illustrative embodiment of a system 100 for removing, or debriding, undesired tissue 102, e.g., necrotic tissue, from a tissue site 104 of a patient is presented. The tissue site 104 is shown as a wound 103 through epidermis 105 and a portion of subcutaneous tissue 107, but the tissue site 104 may be any tissue site that includes a portion that is undesired and which a healthcare provider 112 would like removed. The system 100 uses solid $CO_2$ particles (dry ice) 111 and a working gas to position and cut the undesired tissue 102. The system 100 transports the cut undesired tissue 102 or a portion thereof, which may be referred to as debris 109. The system 100 has little or no distribution of debris 109 at the tissue site 104. The solid $CO_2$ particles 111 may cool the tissue site 104—creating an analgesic effect—to minimize pain experienced by the patient.

The system 100 includes a treatment member 106 that includes a treatment head 108 and may include a handle 110. The treatment member 106 allows the healthcare provider 112 to position the treatment head 108 adjacent to the undesired tissue 102 or a portion thereof for removal. The treatment head 108 has a treatment head body 114 formed with a delivery conduit 116, a treatment cavity 118, and a removal aperture and conduit 120. The treatment cavity 118 formed in the treatment head body 114 is sized and configured to receive the undesired tissue 102 or a portion thereof when the treatment head 108 is placed adjacent the undesired tissue 102 during operation.

The delivery conduit 116 delivers the working gas to the treatment cavity 118 or the working gas and solid $CO_2$ particles 111 to the treatment cavity 118 through a delivery aperture 119. The removal conduit 120 receives the working gas, any additional $CO_2$ in whatever phase the $CO_2$ may be, or debris through a removal orifice 140, or aperture, and transports the contents away. As used herein, unless otherwise indicated, "or" does not require mutual exclusivity. The delivery aperture 119 and the removal orifice 140 may be substantially aligned as shown in FIGS. 1-5 or may have varying angles or degrees of misalignment (see, e.g., FIG. 6), but still suitable to remove debris or gas from the tissue site.

The handle 110, when included, is coupled to the treatment head 108 to form the treatment member 106. The handle 110 may have a handle delivery conduit (not shown) that is fluidly coupled to the delivery conduit 116. The handle 110 may also have a handle removal conduit (not shown) fluidly coupled to the removal conduit 120. The handle delivery conduit and handle removal conduit may be fluidly coupled to a supply conduit 122 and an extraction conduit 124, respectively. Alternatively, the delivery conduit 116 may be fluidly coupled directly to the supply conduit 122 and the removal conduit 120 may be fluidly coupled directly to the extraction conduit 124. The supply conduit 122 and the delivery conduit 116 may be an integral conduit in some embodiments. The supply conduit 122 and the extraction conduit 124 may be two separate conduits, which may be contained within an outer housing conduit 126. Alternatively, the supply conduit 122 and the extraction conduit 124 may be two lumens in a multi-lumen conduit.

The supply conduit 122, which is fluidly coupled to the delivery conduit 116, delivers a working gas alone or a working gas with the solid $CO_2$ particles 111, which may be referred to as a debridement mixture. The working gas is provided by a working gas supply source 128. The working gas supply source 128 is typically a source of pressurized air. Other gases may be used, however, such as carbon dioxide, medical oxygen, or any inert, non-hazardous gas. The working gas is delivered into the supply conduit 122 for eventual introduction by the delivery conduit 116 into the treatment cavity 118. The working gas supply source 128 may be a medical grade air pump or a container of compressed gas. The working gas supply source 128 may regulate the pressure of the working gas by a valve or power control to a pump. The valve or pump may be selectively controlled by a working gas control switch 130 that is coupled by a first control link 132 to the valve or pump of the working gas supply source 128. Thus, the working gas control switch 130 may be moved between a first position and a second position—incrementally or continually—to control the amount of working gas delivered to the treatment cavity 118.

The solid $CO_2$ particles 111 may be selectively introduced into the working gas by a $CO_2$ source 134. The $CO_2$ source 134 is external to the treatment member 106. The $CO_2$ source 134 may maintain the particles in a solid phase—typically around −80° Celsius—and control the rate that the solid $CO_2$ particles 111 are delivered into the working gas in the supply conduit 122. The solid $CO_2$ particles 111 may be any size suitable for removal of the undesired tissue 102. As a non-limiting example, the solid $CO_2$ particles 111 may be in the range of 10 to 1000 microns (μM) or in the range 10 to 100 microns (μM). The $CO_2$ source 134 may include one or more valves or pressure sources for delivering the solid $CO_2$ particles 111 into the working gas in the supply conduit 122 at a selected rate. The valves or pressure sources may be controlled by a $CO_2$ switch 136. The $CO_2$ switch 136 may be coupled by a second link 138 to the valves or pressure sources at the $CO_2$ source 134. In another embodiment, substances in addition to solid $CO_2$, e.g., crystalline anesthetic, may be added to the supply conduit 122. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling means that fluid may be in communication between the designated parts or locations.

After the working gas or debridement mixture enters the treatment cavity 118, the substances may directly traverse the treatment cavity 118 or may impinge upon the undesired tissue 102 within the treatment cavity 118 and thereby create debris 109. When the solid $CO_2$ particles 111 impinge on the undesired tissue 102, the solid $CO_2$ particles 111 typically sublime (go from solid phase to gas phase). Whatever combination of working gas, solid $CO_2$ particles 111, $CO_2$ gas, or debris 109 ("cavity substances") that exists in the treatment cavity 118 is removed through the removal conduit 120 and may initially be received by the removal orifice 140. The removal orifice 140 may be an enlarged portion at a distal end of the removal conduit 120 to help direct the flow into the removal conduit 120. The cavity substances are delivered into the extraction conduit 124.

The extraction conduit 124 may have a reduced pressure as compared to the treatment cavity 118. The reduced pressure may be delivered by the extraction conduit 124 to the removal conduit 120. The reduced pressure may be delivered by a reduced-pressure source 142 to the extraction conduit 124. The reduced-pressure source 142 may be any device for supplying a reduced pressure, such as a vacuum pump, wall suction, or other source. The amount of reduced pressure supplied by the reduced-pressure source 142 may be regulated by valves or a power to a vacuum pump or the like and may be controlled by a reduced-pressure switch 144. The reduced-pressure switch 144 may be coupled to the valves or power of the reduced-pressure source 142 by a third link 146, or coupling.

A collection member 148 may be fluidly coupled to a portion of the extraction conduit 124 to collect the debris 109 and any other solids or liquids in the cavity substances. The collection member 148 may hold, among other things, the debris 109 for testing or disposal.

A master controller 150 may be provided that includes the working gas control switch 130, the $CO_2$ switch 136, and the reduced-pressure switch 144, or any combination of these switches 130, 136, 144. The master controller 150 may be a foot pedal console presenting the healthcare provider 112 with easy access to the switches 130, 136, and 144. The master controller 150 may also be an electronic controller that allows user inputs and helps regulate the three switches 130, 136, and 144 for a desired outcome. Thus, for example, a user may input that soft debridement is desired, such as for sloughly tissue, and a lower pressure of the working gas and smaller solid $CO_2$ particles may be delivered. As another example, the user may input that hard debridement is desired, such as for hard eschar, and a higher pressure and larger solid $CO_2$ particles may be delivered.

In one illustrative embodiment, the healthcare provider 112 uses the treatment member 106 to position the treatment head 108 adjacent to the tissue site 104, and in particular, positions the treatment cavity 118 adjacent to the undesired tissue 102. Either at this time or before, the healthcare provider 112 initiates the delivery of working gas from the working gas supply source 128 to the treatment cavity 118. As the working gas (and other substances) travels from the delivery conduit 116 through the treatment cavity 118 to the removal conduit 120, the relative speed of the working gas compared to fluids at or in the undesired tissue 102 causes the undesired tissue 102 or a portion thereof to enter into the treatment cavity 118. While not limited by theory of operation, the undesired tissue 102 enters the treatment cavity 118 because of a venturi effect or drawing upon Bernoulli's principle. The faster moving fluid causes a low pressure in the treatment cavity 118 that pulls or urges the undesired tissue 102 into the treatment cavity 118. The greater the velocity of the working gas, the greater the force urging the undesired tissue 102 into the treatment cavity 118. Accordingly, the amount of tissue removed may be directly controlled.

Figure 3:
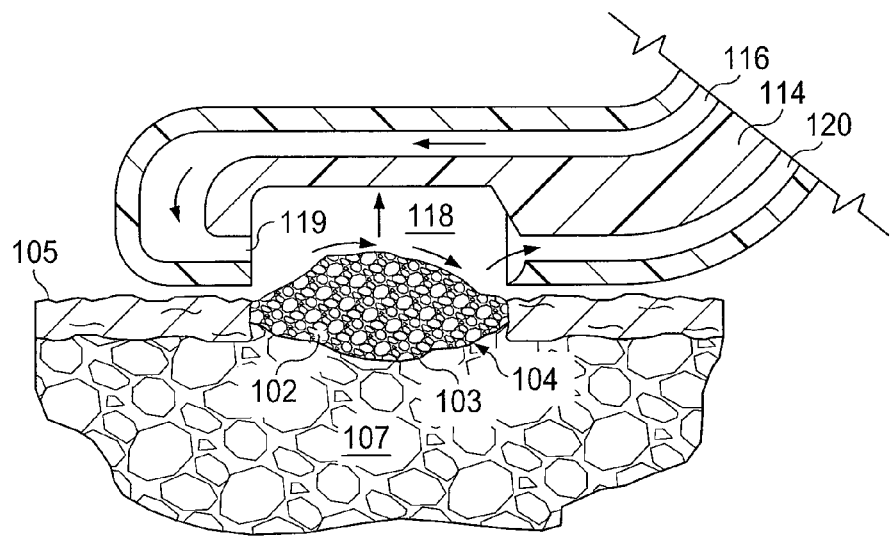
FIG. 3 is a schematic cross section of a portion of the treatment head of the illustrative system shown in FIGS. 1 and 2.
Figure 4:
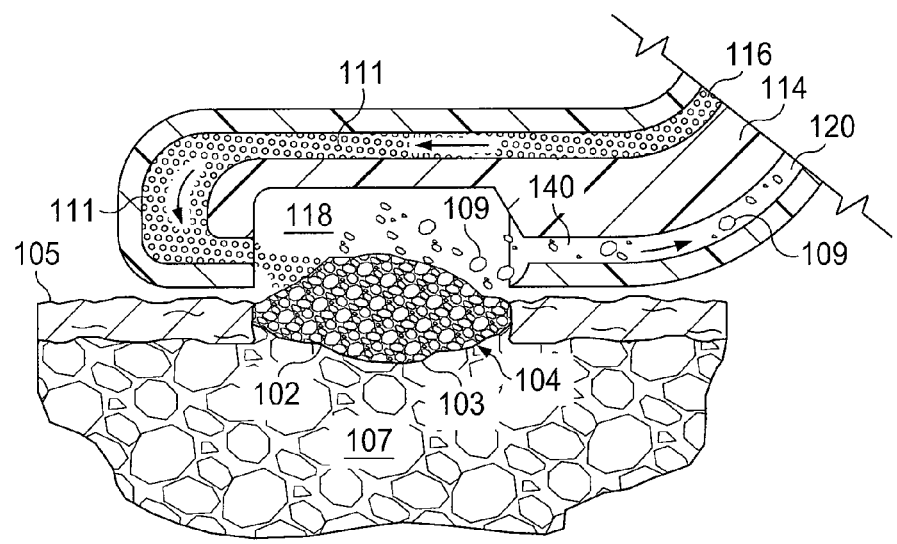
FIG. 4 is a schematic cross section of the treatment head of FIG. 3 shown cutting undesired tissue.

Once the undesired tissue 102 is within the treatment cavity 118 as shown in FIG. 3, the healthcare provider 112 activates the $CO_2$ source 134 and causes the solid $CO_2$ particles 111 to enter the working gas and form a debridement mixture that impinges upon the undesired tissue 102 as shown in FIG. 4. The solid $CO_2$ particles 111 impinge on the undesired tissue 102 and cut portions free to create the debris 109 that is removed. On impact with the undesired tissue 102 or shortly thereafter, the solid $CO_2$ particles 111 sublime to create $CO_2$ gas. The debris 109, working gas, and $CO_2$ gas and any solid $CO_2$ particles enter the removal orifice 140 and the removal conduit 120. The debris 109 is delivered through the extraction conduit 124 to the collection member 148. The debris 109 and other flow may be pulled into the removal orifice 140 by the reduced pressure from the reduced-pressure source 142.

The amount of undesired tissue 102 removed may be controlled using a number of variables: size of the solid $CO_2$ particles 111, number of the solid $CO_2$ particles 111, or pressure of the working gas (and flow rate) from the working gas supply source 128. Another variable may be stated as the pressure gap across the treatment cavity 118, e.g., the pressure differential between the pressure of the working gas supplied by the working gas supply source 128 and the pressure of the reduced-pressure source 142. Lower pressure differential, smaller particle sizes, and fewer particles may used for mild debridement, such as on soft sloughly tissue. Higher pressure differential, larger particle sizes, and more particles may be used on hard eschar tissue. Any combination of these variables may be used to help address different situations. The flow rate of the working gas, the size of solid $CO_2$ particles 111, and the particle feed rate may be controlled to provide cooling of the tissue site 104, which is believed to provide an analgesic effect. The flow rate may be maintained low enough to avoid a cold burn or a penetrating cooling effect to the tissue site 104. A temperature probe, such as a thermistor, may be incorporated at the interface between the treatment head 108 and the epidermis 105 and information from the temperature probe may be used via software control to regulate the size of the solid $CO_2$ particles 111 and the flow of the working gas. In one illustrative, non-limiting embodiment, the flow rate may be provided at a pressure of 1-5 Bar, with solid $CO_2$ particles 111 ranging from a grain of sand to a large pinhead and having a flow rate of 500 g/min in 1-2 $m^3$/min.

FIG. 1 presents a treatment member 106 that uses a plurality of switches 130, 136 to control the working gas flow rate and the solid $CO_2$ particles 111 flow rate, respectively. Referring now primarily to FIG. 5, another illustrative, non-limiting embodiment of a treatment member 206 is presented that may be used with a system, e.g., the system 100 of FIG. 1, for removing, or debriding, undesired tissue, e.g., necrotic tissue, from a tissue site of a patient. The treatment member 206 is analogous in most respects to the treatment member 106 of FIG. 1. The treatment member 206 has a treatment head 208 and a handle 210. The treatment head 208 has a treatment head body 214 formed with a treatment cavity 218.

In this illustrative embodiment, a working gas control switch 230 is on the handle 210. The flow rate (pressure) of working gas delivered to the treatment cavity 218 is controlled by the working gas control switch 230, which may move between a first position and a second position as suggested by arrow 260. The movement of the working gas control switch 230 may provide a variable flow ranging between a no flow condition to maximum flow condition and may do so by continuous control or incremental control. The flow rate of solid $CO_2$ particles is controlled by a $CO_2$ switch 236, which may be a biased trigger. When a healthcare provider is ready to cut tissue pulled into the treatment cavity 218, the healthcare provider pulls the $CO_2$ switch 236 to deliver solid $CO_2$ particles to cut the undesired tissue.

Figure 6:
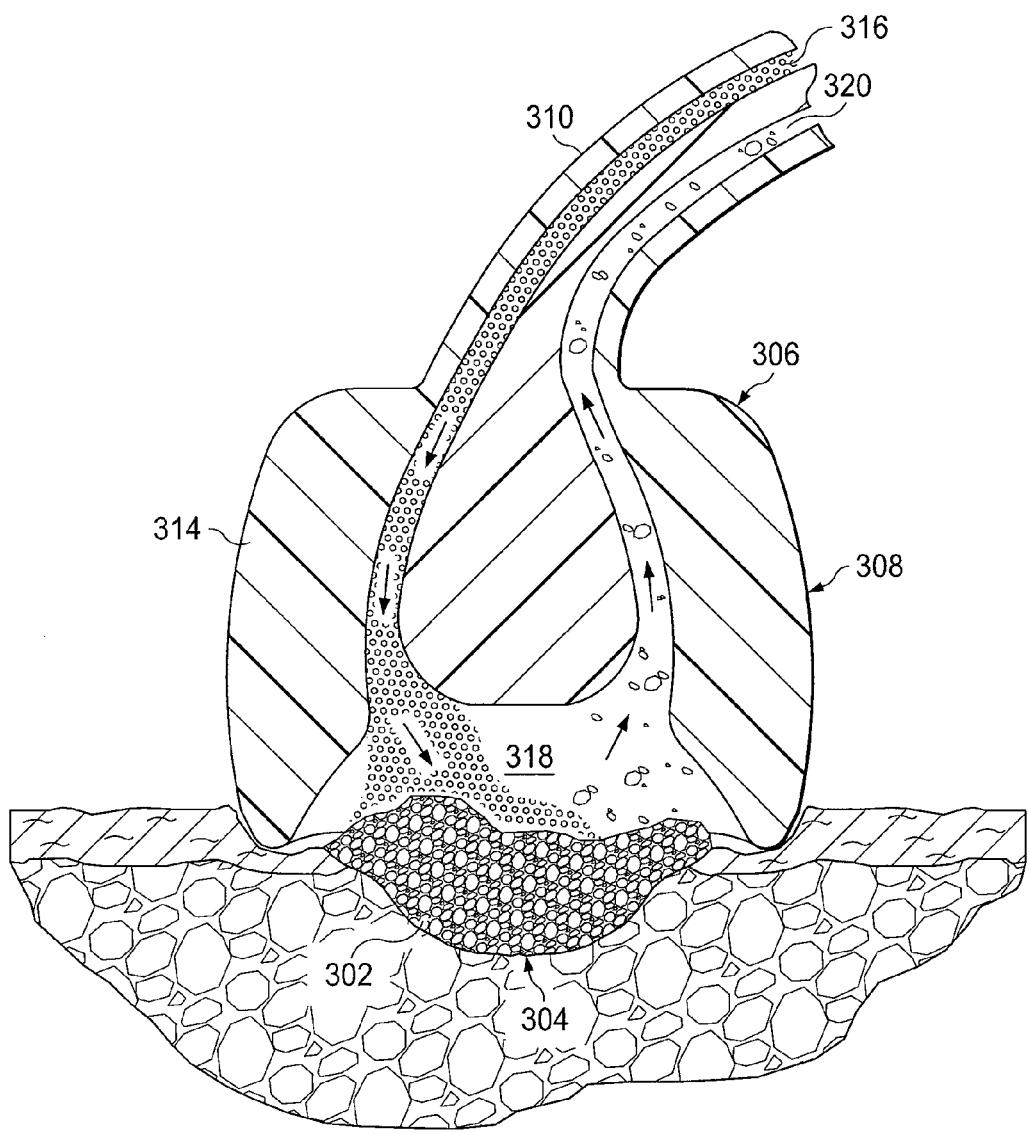
FIG. 6 is a schematic, cross section of another illustrative treatment head of a system for removing undesired tissue from a tissue site.

Referring now primarily to FIG. 6, another illustrative embodiment of a treatment member 306 is presented. The treatment member 306 may be used as part of a system, e.g., the system 100 of FIG. 1, for removing, or debriding, undesired tissue 302, e.g., necrotic tissue, from a tissue site 304 of a patient. The treatment member 306 is analogous in many respects to the treatment member 106 of FIG. 1. The treatment member 306 has a treatment head 308 and a handle 310. The treatment head 308 has a treatment head body 314 formed with a delivery conduit 316, treatment cavity 318, and a removal conduit 320. In this embodiment, however, the delivery conduit 316 is displaced from and not substantially aligned with the removal conduit 320, but is at a different angle—in this example almost 180° different. Thus, a debridement mixture introduced through the delivery conduit 316 impinges on the undesired tissue 302 of the tissue site 304 and then is drawn by reduced pressure into the removal conduit 320 to be transported away for collection or disposal. The angle between the delivery conduit 316 and removal conduit 320 may be substantially 0 (see FIG. 1-4), or 180 (see FIG. 6), or anything in between, e.g., 10°, 20°, 30°, 40°, 50°, 60°, etc. In another embodiment, the angle of impingement on the undesired tissue 302 may be controlled by the healthcare provider. For angles greater than 45°, a reduced pressure system may be necessary to provide suction for removing cavity substances.

Numerous alternatives are possible for the system and methods herein. Referring again to FIGS. 1-4, in an alternative embodiment, the working gas and solid $CO_2$ particles 111 (debridement mixture) may be delivered together from the beginning of the procedure. The debridement mixture urges the undesired tissue 102 into the treatment cavity 118 and cuts (which includes dislodging) the undesired tissue 102 to form the debris 109.

In another alternative embodiment, instead of both the working gas supply source 128 and the reduced-pressure source 142 contributing to the pressure differential across the treatment cavity 118, the pressure differential may be caused only by positive pressure delivered by the working gas supply source 128 or only by the reduced-pressure source 142. In the latter embodiment, a seal or sealing material may be added to provide a fluid seal between the treatment head 108 and the tissue site 104.

In another alternative embodiment, the $CO_2$ source 134 may also allow control of the size of the solid $CO_2$ particles 111 delivered to the treatment cavity 118. Moreover, the $CO_2$ switch 136 may allow selection of particle size in real time or an additional switch may be provided for this purpose.

In another alternative embodiment, a single switch may provide control of the working gas and the solid $CO_2$ particles. In addition, an adjustment switch may set the ratio of working gas and solid $CO_2$ particles, but the rate of delivery may be controlled by a single switch, such as switch 230 in FIG. 5.

According to another illustrative embodiment, a method of debriding undesired tissue from a tissue site includes delivering solid $CO_2$ particles to the undesired tissue so as to cut the undesired tissue. The $CO_2$ particles are allowed to undergo sublimation to produce a $CO_2$ gas. The method further includes removing the $CO_2$ gas and the undesired tissue that has been cut by the solid $CO_2$ particles.

According to another illustrative embodiment, the solid $CO_2$ particles 111 are generated as an aspect of the system 100. In such an illustrative, non-limiting embodiment, a pressurized cylinder containing liquid carbon dioxide and a mechanism of generating $CO_2$ particles through gaseous or liquid conversion are included in the system 100. In this embodiment, dry ice need not be stored or provided.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for removing undesired tissue from a tissue site, the system comprising:
    a treatment head having a first surface, a second surface opposite the first surface, a treatment cavity extending into the treatment head from the second surface, a delivery aperture opening into the treatment cavity, and a removal aperture opening into the treatment cavity, the delivery aperture and the removal aperture face each other and are aligned on at least two orthogonal planes, the removal aperture has a dimension substantially smaller than a dimension of the treatment cavity to form a restricted passage;
    a handle directly coupled to the treatment head to form an obtuse angle with the first surface of the treatment head;
    a working gas supply source adapted to supply a working gas at a positive pressure to the delivery aperture;
    a $CO_2$ source adapted to supply solid $CO_2$ particles having a diameter between about 10 microns and about 1000 microns to the working gas;
    wherein the delivery aperture and the removal aperture are disposed on opposing sides of the treatment cavity and face each other such that movement of the working gas between the delivery aperture and the removal aperture generates a pressure in the treatment cavity that is lower than an ambient pressure that urges uncut undesired tissue into the treatment cavity.

2. The system for removing undesired tissue of claim 1, further comprising:
    a reduced-pressure source for supplying reduced pressure to the treatment head;
    wherein an extraction conduit is fluidly coupled to the reduced-pressure source; and
    wherein the treatment head and the extraction conduit are adapted to carry away the undesired tissue under reduced pressure.

3. The system for removing undesired tissue of claim 1, wherein the $CO_2$ source is operable to control a feed rate of the solid $CO_2$ particles.

4. The system for removing undesired tissue of claim 1, wherein:
    the treatment head further comprises a delivery conduit and a removal conduit;
    the delivery conduit is fluidly coupled to the delivery aperture and the working gas supply source;
    the removal conduit is fluidly coupled to the removal aperture and a reduced-pressure source; and
    the delivery aperture and the removal aperture are substantially aligned.

5. The system for removing undesired tissue of claim 1, wherein the system further comprises a collection member fluidly coupled to the treatment head and a reduced-pressure source to receive the undesired tissue.

6. The system for removing undesired tissue of claim 1, wherein the system further comprises a $CO_2$ switch coupled to the $CO_2$ source, the $CO_2$ switch for controlling a feed rate of the solid $CO_2$ particles from the $CO_2$ source.

7. The system for removing undesired tissue of claim 1, further comprising:
    a master controller associated with the working gas supply source and the $CO_2$ source, the master controller comprising:

a working gas control switch for controlling an amount of the working gas transferred from the working gas supply source to the treatment head, and a $CO_2$ switch for controlling an amount of the solid $CO_2$ particles transferred from the $CO_2$ source into the working gas.

8. The system for removing undesired tissue of claim 1, further comprising:

a foot pedal associated with the working gas supply source and the $CO_2$ source, the foot pedal comprising:

a working gas control switch for controlling an amount of the working gas transferred from the working gas supply source to the treatment head, and a $CO_2$ switch for controlling an amount of the solid $CO_2$ particles transferred from the $CO_2$ source into the working gas.

9. The system for removing undesired tissue of claim 1, further comprising:

a master controller associated with the working gas supply source and the $CO_2$ source, the master controller comprising:

a treatment mixture switch for controlling an amount of the solid $CO_2$ particles and the working gas transferred from the working gas supply source and the $CO_2$ source to the treatment head.

10. A system for removing undesired tissue from a tissue site of a patient, the system comprising:

a working gas supply source adapted to supply a working gas at a positive pressure;

a $CO_2$ source adapted to supply solid $CO_2$ particles;

a supply conduit fluidly coupled to the working gas supply source and the $CO_2$ source for receiving the working gas and solid $CO_2$ particles having a diameter between about 10 microns and about 1000 microns;

a treatment head having a first surface, a second surface opposite the first surface, a treatment cavity extending into the treatment head from the second surface, a delivery aperture opening into the treatment cavity, and a removal aperture opening into the treatment cavity, the delivery aperture and the removal aperture face each other and are aligned on at least two orthogonal planes, the removal aperture has a dimension substantially smaller than a dimension of the treatment cavity to form a restricted passage;

a handle directly coupled to the treatment head to form an obtuse angle with the first surface of the treatment head;

the treatment head fluidly coupled to the supply conduit for receiving the working gas and solid $CO_2$ particles and delivering the working gas and solid $CO_2$ particles to the tissue site at a desired location;

wherein the delivery aperture and the removal aperture are substantially aligned on opposing sides of the treatment cavity and face each other such that movement of the working gas between the delivery aperture and the removal aperture generates a pressure in the treatment cavity that is lower than an ambient pressure that urges uncut undesired tissue into the treatment cavity; and wherein the treatment head is adapted to cause the solid $CO_2$ particles to impinge upon at least a portion of the undesired tissue in the treatment cavity so as to remove the undesired tissue.

* * * * *